(12) United States Patent
Dalke

(10) Patent No.: US 9,354,267 B1
(45) Date of Patent: May 31, 2016

(54) SENSOR PROBE ASSEMBLY

(75) Inventor: Dale Dalke, Thousand Oaks, CA (US)

(73) Assignee: Neurotopia, Inc., Atascadero, CA (US)

( * ) Notice: Subject to any disclaimer, the term of this patent is extended or adjusted under 35 U.S.C. 154(b) by 112 days.

(21) Appl. No.: 13/551,770

(22) Filed: Jul. 18, 2012

(51) Int. Cl.
 *G01R 31/02* (2006.01)
(52) U.S. Cl.
 CPC .................................. *G01R 31/02* (2013.01)
(58) Field of Classification Search
 CPC ... G01R 1/067; G01R 1/06788; A61B 5/0478
 USPC .................. 324/149, 754.01, 754.03, 754.11,
 324/755.01, 755.11, 756.04; 600/383, 544,
 600/378, 395, 385
 See application file for complete search history.

(56) References Cited

U.S. PATENT DOCUMENTS

| | | | | |
|---|---|---|---|---|
| 4,461,304 | A * | 7/1984 | Kuperstein | 600/378 |
| 4,928,704 | A | 5/1990 | Hardt | |
| 5,731,710 | A * | 3/1998 | Mizuno et al. | 324/754.2 |
| 5,899,867 | A | 5/1999 | Collura | |
| 6,181,149 | B1 * | 1/2001 | Godfrey et al. | 324/750.19 |
| 6,194,908 | B1 * | 2/2001 | Wheel et al. | 324/756.04 |
| 6,254,536 | B1 | 7/2001 | DeVito | |
| 6,450,820 | B1 | 9/2002 | Palsson et al. | |
| 6,996,261 | B2 | 2/2006 | deCharms | |
| 7,983,762 | B2 | 7/2011 | Gliner et al. | |
| 7,990,156 | B1 * | 8/2011 | Watkins, Jr. | 324/551 |
| 2002/0175695 | A1 * | 11/2002 | Ahmann et al. | 324/761 |
| 2009/0069707 | A1 | 3/2009 | Sandford | |
| 2010/0217099 | A1 | 8/2010 | LeBoeuf et al. | |
| 2010/0297863 | A1 * | 11/2010 | Eldridge | 439/197 |
| 2011/0054342 | A1 | 3/2011 | Matthews, Jr. | |
| 2011/0054649 | A1 | 3/2011 | Sarkis et al. | |
| 2011/0183305 | A1 | 7/2011 | Orbach | |
| 2011/0270074 | A1 | 11/2011 | deCharms | |
| 2012/0021394 | A1 | 1/2012 | deCharms | |
| 2012/0071947 | A1 | 3/2012 | Gupta et al. | |
| 2012/0077160 | A1 | 3/2012 | DeGutis et al. | |
| 2012/0092618 | A1 | 4/2012 | Yoo et al. | |
| 2012/0100514 | A1 | 4/2012 | Desain et al. | |
| 2012/0130205 | A1 | 5/2012 | Burton et al. | |

* cited by examiner

*Primary Examiner* — Arleen M Vazquez
*Assistant Examiner* — Brent J Andrews
(74) *Attorney, Agent, or Firm* — Hall Estill Attorneys at Law; Daniel P. Dooley

(57) ABSTRACT

Preferably, an embodiment of a sensor probe assembly includes at least a conductive pin securement member, and a multitude of conductive pins cooperating with the conductive pin securement member. Each conductive pin has a multitude of degrees of freedom relative to, as well as separate and distinct from, each of the remaining plurality of conductive pins. More preferably, an embodiment of a sensor probe assembly includes at least a flexible, electrically conductive pin securement member formed from a polymer filled with conductive particles. Interacting with the flexible, electrically conductive pin securement member is a plurality of electrically conductive pins, wherein each electrically conductive pin has a multitude of degrees of freedom relative to each of the remaining plurality of conductive pins, and cooperates with the electrically conductive pin securement member in a pressing engagement relationship.

19 Claims, 4 Drawing Sheets

FIG. 9
FIG. 10
FIG. 11
FIG. 12
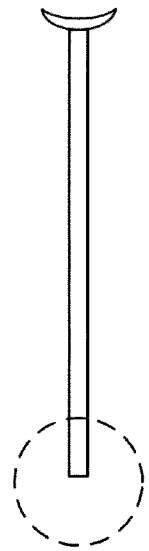
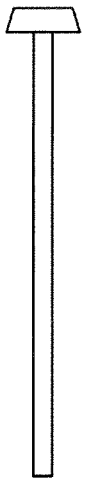
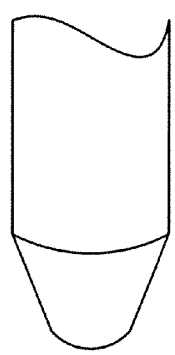
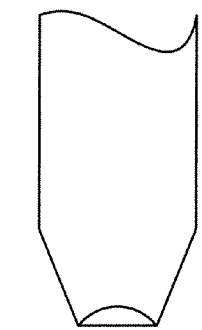
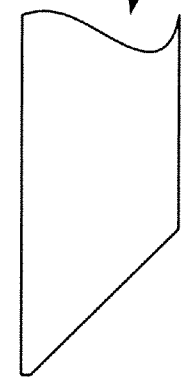
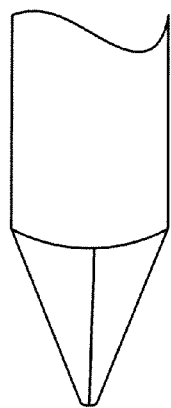
FIG. 13
FIG. 14
FIG. 15
FIG. 16

SENSOR PROBE ASSEMBLY

FIELD OF THE INVENTION

The present invention relates to the field of sensors. More particularly, the present invention relates to sensor probe assemblies.

BACKGROUND OF THE INVENTION

The present invention relates to sensor probe assemblies for use in recording neurophysiological signals. Prior art sensor probe assemblies, have for the most part, depended on the preparation of an area of interest on a cranium of a subject, application of a gel like conductive material, and attachment of the probe to the cranium of the subject at the prepared and gelled site.

As advancements have been made in the field of electronics, it has become desirable to obtain neurophysiological signal data from subjects external to a laboratory or testing facility environment, without the need to prepare and gel a site of interest. Accordingly, improvements in apparatus and methods of providing sensor probes are needed and it is to these needs the present invention is directed.

SUMMARY OF THE INVENTION

In accordance with preferred embodiments, a sensor probe assembly preferably includes at least a conductive pin securement member, and a plurality of conductive pins cooperating with the conductive pin securement member, wherein each conductive pin has a plurality of degrees of freedom relative to, as well as separate and distinct from each of the remaining plurality of conductive pins.

In an alternate preferred embodiment, a sensor probe assembly incorporates at least a flexible, electrically conductive pin securement member formed from a polymer filled with conductive particles. Preferably, cooperating with the flexible, electrically conductive pin securement member is a plurality of electrically conductive pins, wherein each electrically conductive pin has multiple degrees of freedom relative to, as well as separate and distinct from, each of the remaining plurality of conductive pins. Further preferably, each of the electrically conductive pin cooperates with the flexible, electrically conductive pin securement in a pressing engagement relationship.

These and various other features and advantages that characterize the claimed invention will be apparent upon reading the following detailed description and upon review of the associated drawings.

BRIEF DESCRIPTION OF THE DRAWINGS

The present invention is illustrated by way of example and not limitation in the figures of the accompanying drawings, in which like references indicate similar elements and in which:

FIG. 9 is a front elevation view of an embodiment exemplary of an electrically conductive pin of FIG. 6, showing a head portion, a tip portion, and a body portion disposed there between.

FIG. 10 is a front elevation view of an embodiment exemplary of an electrically conductive pin of FIG. 2, showing a head portion having a convex shape, a tip portion, and a body portion disposed there between.

FIG. 11 is a front elevation view of an alternate embodiment exemplary of an electrically conductive pin of FIG. 2, showing a head portion having a concave shape, a tip portion, and a body portion disposed there between.

FIG. 12 is a front elevation view of an embodiment exemplary of an electrically conductive pin of FIG. 2, showing a head portion having a substantially flat top surface, a tip portion, and a body portion disposed there between.

FIG. 13 is a partial cutaway front elevation view of an alternate tip configuration for any of the electrically conductive pins of FIG. 9, 10, 11, or 12.

FIG. 14 is a cross-section, partial cutaway front elevation view of an alternate tip configuration for any of the electrically conductive pins of FIG. 9, 10, 11, or 12.

FIG. 15 is a partial cutaway front elevation view of an alternative tip configuration for any of the electrically conductive pins of FIG. 9, 10, 11, or 12.

FIG. 16 is a partial cutaway front elevation view of an alternate tip configuration for any of the electrically conductive pins of FIG. 9, 10, 11, or 12.

DESCRIPTION OF PREFERRED EMBODIMENTS

It will be readily understood that elements of the present invention, as generally described and illustrated in the figures herein, could be arranged and designed in a wide variety of different configurations. Referring now in detail to the drawings of the preferred embodiments, a sensor probe assembly 10, of FIG. 1, (also referred to herein as assembly 10) of a first preferred embodiment, while useable for a wide variety of bio-physiological sensing applications, it is particularly adapted for use as neurophysiological signal sensor component. Accordingly, the assembly 10 of the first preferred embodiment, of FIG. 1, will be described in conjunction with the merits of the use of the sensor probe assembly 10 as a neurophysiological signal sensor component.

Figure 1:
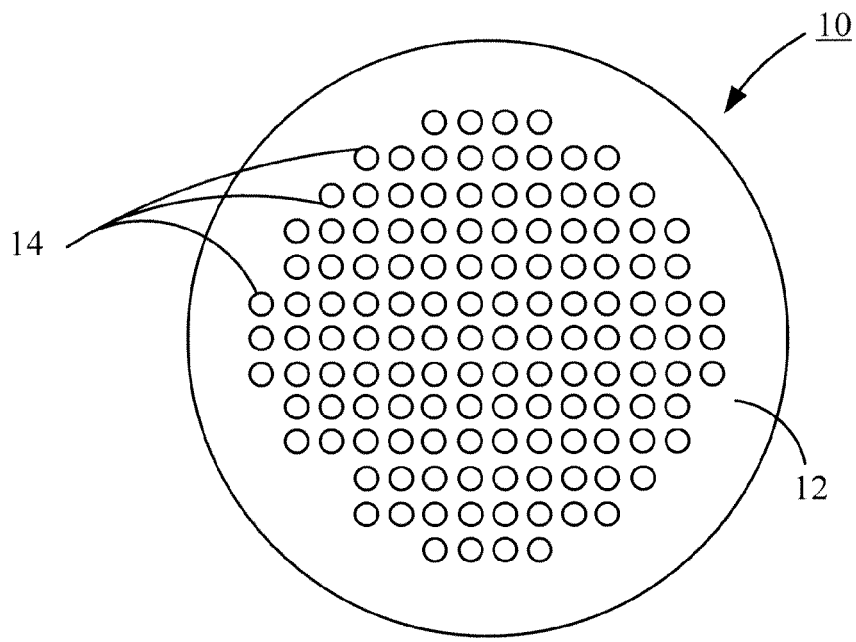
FIG. 1 is a top plan view of an embodiment exemplary of the inventive sensor probe assembly.
Figure 3:
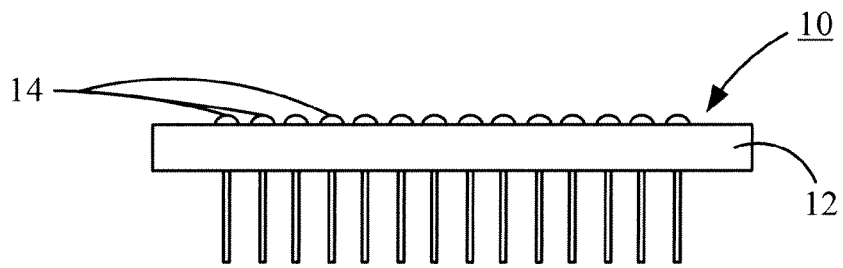
FIG. 3 is a front side view in elevation of an embodiment exemplary of the inventive sensor probe assembly of FIG. 1.

In a preferred embodiment of FIG. 1, the sensor probe assembly 10 includes at least a conductive pin securement member 12, which hosts a plurality of conductive pins 14. Preferably, the plurality of conductive pins 14 are electrically conductive, and when in pressing contact with the conductive pin securement member 12, as shown by FIG. 3, form the sensor probe assembly 10 that yields a low impedance neurophysiological signal sensor component.

Figure 2:
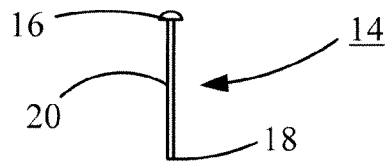
FIG. 2 is a view in elevation of an embodiment exemplary of a conductive pin of the inventive sensor probe assembly of FIG. 1.

In a preferred embodiment, the conductive pins 14, an example of which is shown by FIG. 2, include at least a head portion 16, a tip portion 18, and a body portion 20 disposed between the head portion 16 and the tip portion 18. Preferably, each conductive pin 14 is formed from a non-corrosive material, such as stainless steel, titanium, bronze, or a gold plating on a rigid substrate selected from a group including at least polymers and metals. Preferably, the head portion 16 has a diameter greater than the diameter of the body portion 20.

Figure 4:
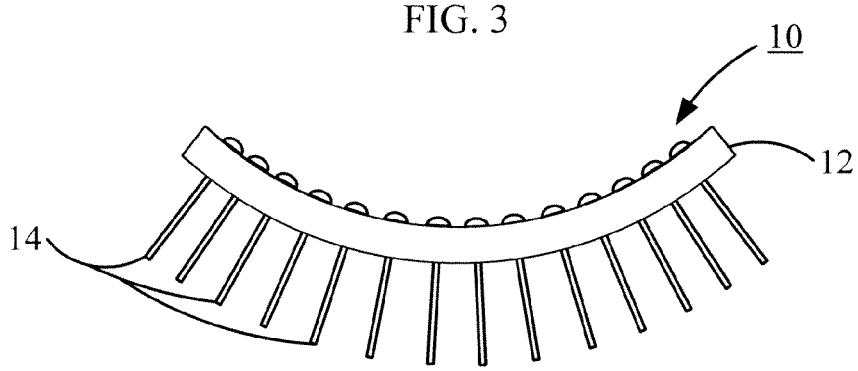
FIG. 4 is a front side view in elevation of an embodiment exemplary of the inventive sensor probe assembly illustrative of a flexible, electrically conductive pin securement member and associated plurality of electrically conductive pins matted thereto, of an embodiment exemplary of the inventive sensor probe assembly of FIG. 1.

As shown by FIG. 4, the conductive pin securement member 12 is preferably flexible and formed from a polymer. The electrical conductivity of the conductive pin securement member 12 is preferably attained by the inclusion of conductive particles embedded within the polymer. One such combination is a carbon filed silicon sheet material provided by Stockwell Elastomerics, Inc. of Philadelphia, Pa. However, as known in the art, conductive polymers may be formed from a plurality of polymer materials filled with conductive particles, the shape of which may be formed using well known manufacturing techniques that include at least molding, extrusion dies and sliced to thickness, formed in sheets and: die cut; cut with hot wire equipment; high pressure water jets, or steel rule dies.

Figure 5:
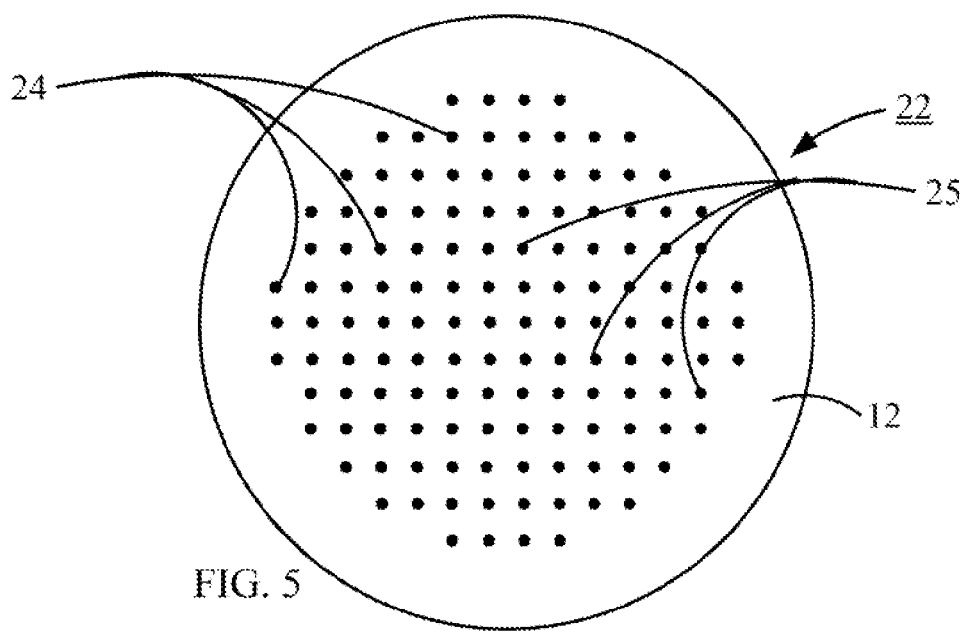
FIG. 5 is a top plan view of an alternate embodiment exemplary of the inventive sensor probe assembly.
Figure 6:
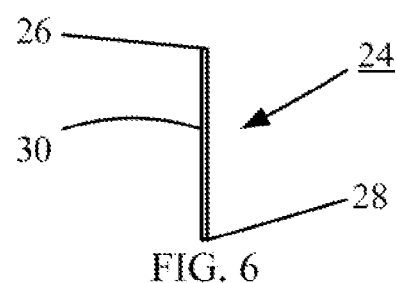
FIG. 6 is a view in front elevation of an alternate embodiment exemplary an electrically conductive pin of the inventive sensor probe assembly of FIG. 5.

FIG. 5 shows an alternate embodiment of a sensor probe assembly 22, which is preferably formed from the flexible, electrically conductive pin securement member 12, and a plurality of alternate preferred conductive pins 24 cooperating with a corresponding securement pass through aperture 25. The plurality of securement pass through apertures 25 are provided by the flexible, electrically conductive pin securement member 12. As shown by FIG. 6, preferably each alternate preferred conductive pin 24 includes a head portion 26, a tip portion 28, and a body portion 30, wherein the head portion 26 and the tip portion 28 have diameters substantially equal to the body portion 30. However, a skilled artisan will appreciate that conductive pins may have head, tip and body portion diameters different from one another. For example, the body portion may have a diameter greater than either the tip portion or head portion to accommodate insert molding of the conductive pins into a conductive pin securement member. It is further understood that the conductive pins may take on a profile that includes a bend in the body, tip, or head portions, as opposed to the cylindrical configuration of any suitable cross section geometric shape of the conductive pins shown by FIG. 2 and FIG. 6. It is still further understood, that the conductive pins may be formed by a plurality of individual components, including without limitation a spring, or may be formed from a coiled or other form of spring alone.

As with the preferred conductive pins 14, the alternate preferred conductive pins 24 are formed from a non-corrosive material, such as stainless steel, titanium, bronze, or a precious metal plating on a rigid substrate selected from a group including at least polymers and metals.

Figure 7:
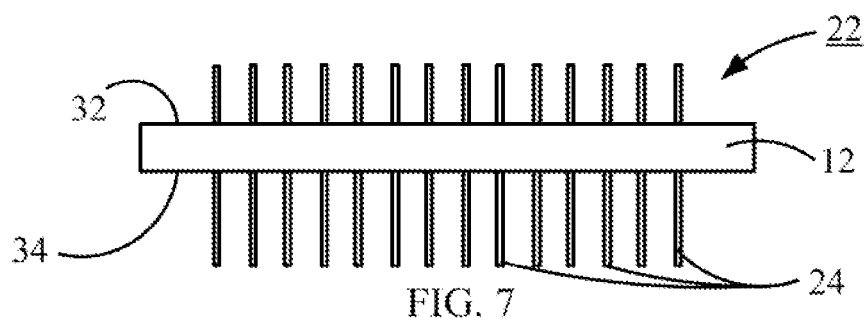
FIG. 7 is a front side view in elevation of an alternate embodiment exemplary of the inventive sensor probe assembly of FIG. 5.
Figure 8:
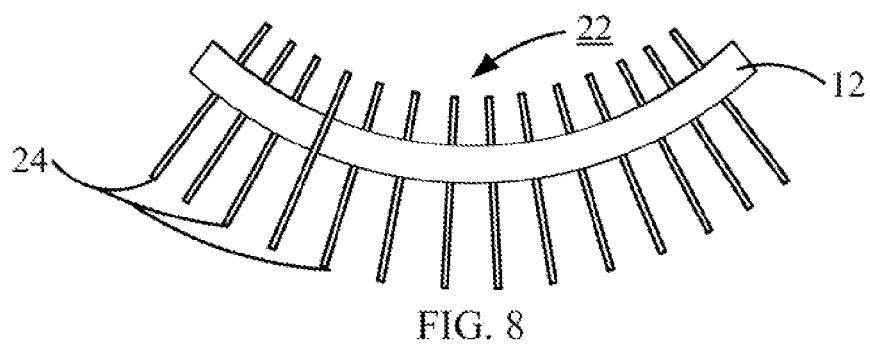
FIG. 8 is a front side view in elevation of an alternate embodiment exemplary of the inventive sensor probe assembly illustrative of a flexible, electrically conductive pin securement member and associated plurality of electrically conductive pins matted thereto, of an embodiment exemplary of the inventive sensor probe assembly of FIG. 5.

FIG. 7 shows the conductive pins 24 protruding through each the top and bottom surfaces, 32 and 34 respectfully, to accommodate improved conductivity of the alternate sensor probe assembly 22, with mating components. While FIG. 8 shows that the alternate sensor probe assembly 22 preferably retains the flexibility characteristics of sensor probe assembly 10 of FIG. 4.

FIGS. 9, 10, 11, and 12 show just a few of a plurality of head configurations suitable for use on conductive pins. The particular configuration selected is a function of the device or component with which the conductive pins electrically cooperate. When a connector is used to interface with the sensor probe assembly, such as 10 or 22, the precise configuration will depend on the type and configuration of the pins associated with the connector, including whether the pins are male or female pins.

FIGS. 13, 14 (a cross section view), 15, and 16 show just a few of a plurality of tip configurations suitable for use on conductive pins. The particular configuration selected is a function of the materials used to form the conductive pins, and the environment in which the conductive pin will be placed. Examples of the use environment include where on the cranium the sensor will be placed, whether hair is present, and the sensitivity of the subject to the tips of the conductive pins.

Figure 17:
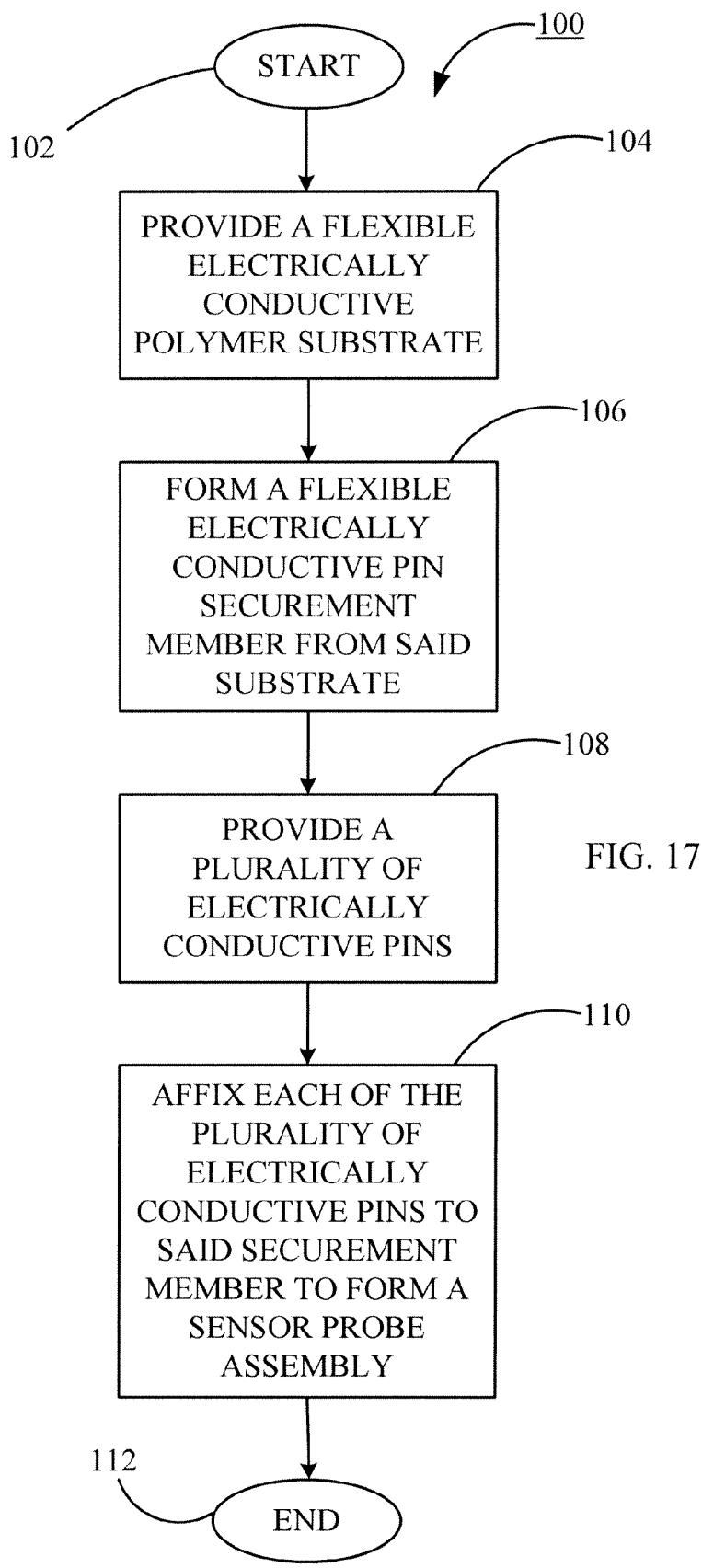
FIG. 17 is a flowchart of a method of producing an embodiment exemplary of the inventive sensor probe assembly of either FIG. 1 or FIG. 5.

FIG. 17 shows a method 100, of making a sensor probe assembly, such as 10 or 22. The method begins at start step 102, and proceeds to process step 104, where a flexible conductive pin securement material is provided (also referred to herein as a flexible, electrically conductive, polymer substrate). At process step 106, a flexible, electrically conductive, pin securement member (such as 12) is formed from the flexible, electrically conductive, polymer substrate.

The process continues at process step 108, a plurality of electrically conductive pins (such as 14) is provided. At process step 110, each of the plurality of electrically conductive pins are affixed to the flexible, electrically conductive, pin securement member, and the process concludes at end process step 112 with the formation of a sensor probe assembly.

As will be apparent to those skilled in the art, a number of modifications could be made to the preferred embodiments which would not depart from the spirit or the scope of the present invention. While the presently preferred embodiments have been described for purposes of this disclosure, numerous changes and modifications will be apparent to those skilled in the art. Insofar as these changes and modifications are within the purview of the appended claims, they are to be considered as part of the present invention.

What is claimed is:

1. A sensor probe assembly comprising:
    a flexible, electrically conductive pin securement member, the flexible, electrically conductive pin securement member provides a plurality of pin securement pass through apertures; and
    a plurality of electrically conductive pins, in which the plurality of electrically conductive pins is not less than three electrically conductive pins, each of the plurality of electrically conductive pins cooperating with a corresponding securement pass through aperture of the plurality of securement pass through apertures forms a highly conductive, low impedance neurophysiological signal sensor component, wherein each electrically conductive pin, along a full length of its entirety, has a plurality of degrees of freedom relative to, as well as independent, separate and distinct from, each of the remaining plurality of electrically conductive pins, the flexible, electrically conductive pin securement member provides a direct electrical connection between and among each of the plurality of electrically conductive pins, such that when any of the plurality of electrically conductive pins are in electrical contact with the flexible, electrically conductive pin securement member, the highly conductive, low impedance neurophysiological signal sensor component is formed from the union of the plurality of electrically conductive pins with the flexible, electrically conductive pin securement member, and wherein each of the electrically conductive pins of the plurality of electrically conductive pins is electrically conductive, formed from a polymer filled with conductive particles, and comprises a head portion, a tip portion, and a body portion disposed between the head portion and the tip portion, and in which each the head portion, tip portion, and body portion are formed from the polymer filled with conductive particles.

2. The sensor probe assembly of claim 1, wherein the flexible, electrically conductive pin securement member is highly conductive, and in which each of the plurality of electrically conductive pins cooperates with the flexible, electrically conductive pin securement member in a pressing engagement relationship.

3. The sensor probe assembly of claim 1, wherein the flexible, electrically conductive pin securement member is highly conductive, and in which each of the plurality of electrically conductive pins cooperates with the flexible, electrically conductive pin securement member in a slip fit relationship.

4. The sensor probe assembly of claim 1, wherein the flexible, electrically conductive pin securement member is conductive, and in which each of the plurality of electrically conductive pins cooperates with the flexible, electrically conductive pin securement member in a sliding engagement relationship.

5. The sensor probe assembly of claim 1, wherein the flexible, electrically conductive pin securement member is formed from an electrically conductive material of predetermined impedance when in a circuit cooperating in electrical contact with the plurality of electrically conductive pins.

6. The sensor probe assembly of claim 5, wherein the electrically conductive material is formed from a polymer filled with conductive particles.

7. The sensor probe assembly of claim 6, wherein the conductive particles comprise carbon.

8. The sensor probe assembly of claim 1, wherein the flexible, electrically conductive pin securement member is a flexible electrically conductive material of predetermined impedance when in a circuit cooperating with the plurality of electrically conductive pins.

9. The sensor probe assembly of claim 8, wherein the electrically conductive material is formed from a polymer filled with conductive particles.

10. The sensor probe assembly of claim 9, in which the polymer is silicon.

11. The sensor probe assembly of claim 10, wherein the conductive particles comprise carbon.

12. The sensor probe assembly of claim 1, in which the head portion has a diameter greater than a diameter of the body portion.

13. The sensor probe assembly of claim 12, in which the head portion presents a convex top surface.

14. The sensor probe assembly of claim 12, in which the head portion presents a concave top surface.

15. The sensor probe assembly of claim 12, in which the head portion presents a substantially flat top surface.

16. The sensor probe assembly of claim 12, in which the tip portion presents a convex bottom surface.

17. The sensor probe assembly of claim 12, in which the tip portion presents a concave bottom surface.

18. The sensor probe assembly of claim 12, in which the tip portion presents a substantially pointed bottom surface.

19. A sensor probe assembly comprising:
  a flexible, electrically conductive pin securement member formed from a polymer filled with conductive particles, the flexible, electrically conductive pin securement member provides a plurality of pin securement pass through apertures; and
  a plurality of electrically conductive pins, in which the plurality of electrically conductive pins is not less than three electrically conductive pins, each of the plurality of electrically conductive pins cooperating with a corresponding securement pass through aperture of the plurality of securement pass through apertures of the flexible, electrically conductive pin securement member forms a highly conductive, low impedance neurophysiological signal sensor component, wherein each electrically conductive pin, along a full length of its entirety, has a plurality of degrees of freedom relative to, as well as independent, separate and distinct from, each of the remaining plurality of electrically conductive pins, each of the electrically conductive pin cooperates with the flexible, electrically conductive pin securement member in a pressing engagement relationship, the flexible, electrically conductive pin securement member provides a direct electrical connection between and among each of the plurality of electrically conductive pins, such that the highly conductive, low impedance neurophysiological signal sensor component is formed from the union of the plurality of electrically conductive pins with the flexible, electrically conductive pin securement member, and wherein each of the electrically conductive pins of the plurality of electrically conductive pins is electrically conductive, formed from a polymer filled with conductive particles, and comprises a head portion, a tip portion, and a body portion disposed between the head portion and the tip portion, and in which each the head portion, tip portion, and body portion are formed from the polymer filled with conductive particles.

\* \* \* \* \*